(12) United States Patent
Sato

(10) Patent No.: US 6,197,284 B1
(45) Date of Patent: Mar. 6, 2001

(54) LIPCOLOR COMPOSITION

(75) Inventor: Nobumasa Sato, Odawara (JP)

(73) Assignee: Kanebo, Ltd., Tokyo (JP)

( * ) Notice: Subject to any disclaimer, the term of this patent is extended or adjusted under 35 U.S.C. 154(b) by 0 days.

(21) Appl. No.: 08/031,596

(22) Filed: Mar. 15, 1993

(51) Int. Cl.⁷ ............................. A61K 7/027; A61K 7/025
(52) U.S. Cl. ................................... 424/64; 424/63
(58) Field of Search ..................... 424/64, 63; 106/404

(56) References Cited

U.S. PATENT DOCUMENTS

| | | |
|---|---|---|
| 4,795,631 | 1/1989 | Sheehan . |
| 5,108,737 * | 4/1992 | Dunphy et al. ................ 424/64 |
| 5,141,741 * | 8/1992 | Isida et al. .................... 424/64 |
| 5,165,915 * | 11/1992 | Tokubo et al. ................ 424/64 |
| 5,176,902 * | 1/1993 | Castro et al. ................. 424/63 |

FOREIGN PATENT DOCUMENTS

| | | |
|---|---|---|
| 0549267 | 6/1993 | (EP) . |
| 2604625 | 4/1988 | (FR) . |
| 1096111 * | 4/1989 | (JP) . |

OTHER PUBLICATIONS

Patent Abstract of Japan vol. 13, No. 308 (c–617) JP–A–01 096 111 (Kanebo Ltd.).
Patent Abstract of Japan vol. 12, No. 491 (c–554) JP–A–63 201 109 (Kobayashi Kooc K.K.).

* cited by examiner

*Primary Examiner*—Robert H. Harrison
(74) *Attorney, Agent, or Firm*—Pitney, Hardin, Kipp & Szuch LLP

(57) ABSTRACT

Lipcolor comprising a salt or hydroxide of di-or trivalent metal, a water-soluble alginate, a red or orange lake color having a COONa or COOK group, and an oil coponent having appearance of liquid at 20° C. The lipcolor less yields a dry feeling or an uneasy feeling with the passage of time, and its color comes off less in friction with foods and drinks.

9 Claims, No Drawings

LIPCOLOR COMPOSITION

FIELD OF THE INVENTION

The present invention relates to a lipcolor composition, particularly a lipcolor composition which less yields a dry feeling and an uneasy feeling with the passage of time, and whose color comes off less in friction with foods, drinks and so on.

BACKGROUND OF THE INVENTION

Lipcolors intrinsically function to make up lips, make a complexion better and make an expression brighter. Now, the increasing number of women have jobs and are working actively. Lipcolors play a very important role in makeup effects, compared to other makeup cosmetics, as a lipcolor alone can produce a bright expression even without a makeup base or other cosmetics. Accordingly, many working women tend to just arrange hair styles, pencil eyebrows and put on lipcolor. Then, busy women want to save time of fixing their lipcolor and are interested in durability of makeup effects more than ever. However, lipcolor compositions without an oil component and a coloring component were hardly conceivable from a point of view of satisfactory makeup effects and physical feelings. Accordingly, only limited means were allowed to enhance durability of the makeup effects. That is, most popular ways are to blend a large amount of a highly sticky or solid oil component or a coloring agent, or to blend a coloring substance having a dyeing property. There is a little elaborate method where a volatile component is blended and, upon its volatization, there remain only a powdery component, a solid oil component and a highly sticky oil component. Unfortunately, lipsticks produced in these methods are not durable to friction with foods, drinks and so on, loose their comfortable feeling of use and tend to discolor and cause a dry feeling with the passage of time. Thus, intrinsic functions of lipsticks are lost easily.

The present inventor proposed oily makeup cosmetics comprising divalent or trivalent metal or its salt or hydroxide, a water-soluble salt of alginic acid and an oil component (Japanese Patent Application Laid-Open Hei-1-96111). The oil components described there are olive oil, castor oil, jojoba oil, lanoline, vaseline, squalane, liquid paraffin, octyl dodecanol, glyceryl tri(caprylate/caprate) and silicone oil. The oily makeup cosmetics include a lipstick which comprises D. & C. Red No. 7 (C.I. No. 15850) (see the present specification, Comparison Example 4) and Aluminium lake of F.D. & C. Yellow No. 5 (C.I. No. 19140); candelilla wax, carnauba wax, vaseline, lanoline, octyl dodecanol and castor oil; calcium pantothenate, calcium lactate or calcium sulfate; and sodium alginate.

SUMMARY OF THE INVENTION

A purpose of the invention is to provide a lipcolor composition which less yields a dry feeling and an uneasy feeling with the passage of time and whose color comes off less in friction with foods, drinks and so on.

The present invention is a lipcolor composition comprising (a) at least one metal compound selected from the group consisting of salts of divalent and trivalent metals and hydroxides of divalent and trivalent metals, and (b) a water-soluble salt of alginic acid, characterized in that the composition further comprises (c) at least one red or orange lake color having a COONa or COOK group in its structure and (d) an oil component having appearance of liquid at a temperature of 20° C.

PREFERRED EMBODIMENTS OF THE INVENTION

The salts of divalent or trivalent metals used in the invention are known. Examples of the salts include calcium chloride, calcium carbonate, calcium lactate, calcium pantothenate, calcium sulfate, calcium citrate, calcium glycerophosphate, calcium gluconate, calcium hydrogenpyrophosphate, calcium biphosphate, calcium silicate, calcium stearate, calcium mesotartrate, calcium laurate, calcium acetate, aluminium sulfate, aluminium chloride, potassium alum, ferrous sulfate, ferric chloride, ferrous or ferric citrate, ferrous or ferric lactate, ferrous pyrophosphate, and sodium ferrous citrate. Water-insoluble salts such as barium sulfate are not preferred as they hardly react on lips. Hardly soluble salts such as calcium sulfate may be used. Preferred are calcium lactate, calcium pantothenate and calcium sulfate. The hydroxides of divalent or trivalent metals include calcium hydroxide, aluminium hydroxide and ferrous hydroxide.

The water-soluble salt of alginic acid used in the invention is known and includes sodium alginate, potassium alginate and ammonium alginate. The molecular weight of alginic acid is preferably 50,000 to 200,000, particularly 100,000 to 200,000, but not limited to these. The use of the higher molecular weight gives better results in the invention.

The red or orange colors having a COONa or COOK group in their structure are known. Those having a COONa group include D. & C. Red No. 28 (C.I. No. 45410); Rose bengal (C.I. No. 45440); D. & C. Red No. 22 (C.I. No. 45380); and D. & C. Orange No. 11 (C.I. No. 45425). Those having a COOK group include Eosine YSK (C.I. No. 45380); Phloxine BK (C.I. No. 45410); and Rose bengal K (C.I. No. 45440). The lakes of the colors used in the invention are lakes of the aforesaid colors with aluminium, barium, or zirconium the like.

The oil component which has appearance of liquid at a temperature of 20° C. includes monohydric alcohols having at least 16 carbon atoms; esters of monohydric alcohols having at least 3 carbon atoms or cholesterols with monobasic aliphatic carboxylic acids having at least 8 carbon atoms, adipic acid, oxystearic acid, succinic acid or malic acid; and esters of ethylene glycol, propylene glycol, neopentyl glycol, glycerin, diglycerin, trimethylol propane or pentaerythrytol with monobasic aliphatic carboxylic acids having at least 7 carbon atoms.

The monohydric alcohols having at least 16 carbon atoms, which have appearance of liquid at 20° C. and are used in the invention, are known and include isosteary alcohol, 2-octyl dodecanol, oleyl alcohol, 2-hexyl decanol and jojoba alcohol.

The ester of monohydric alcohols having at least 3 carbon atoms or cholesterols with monobasic aliphatic carboxylic acids having at least 8 carbon atoms, adipic acid, oxystearic acid, succinic acid or malic acid, which have appearance of liquid at 20° C. and are used in the invention, are known and include diisostearyl adipate, dioctyl adipate, isopropyl isostearate, cholesteryl isostearate, isononyl isononanoate, octyldodecyl erucate (ester of erucic acid), octyl oxystearate, cetyl octanoate, octyldodecyl oleate, oleyl oleate, dioctyl succinate, isocetyl stearate, isopropyl palmitate, octyldodecyl myristate, myristyl myristate, diisostearyl malate, decyl oleate, and octyldodecyl ricinoleate.

The esters of ethylene glycol, propylene glycol, neopentyl glycol, glycerin, diglycerin, trimethylol propane or pentaerythrytol with monobasic aliphatic carboxylic acids having at least 7 carbon atoms, which have appearance of liquid at 20° C. and are used in the invention, are known and include ethylene glycol octanoate, ethyleneglycol palmitate, propylene glycol isostearate, propylene glycol ricinoleate, propylene glycol di(caprylate/caprate), propylene glycol dicaprylate, propylene glycol dimyristate, propylene glycol dicaprate, neopentyl glycol dioctanoate, neopentyl glycol dicaprate, glyceryl triisostearate, glyceryl diisoastearate, glyceryl trioctanoate, glyceryl tri (caprylate/caprate), glyceryl ricinoleate, diglyceryl isostearate, diglyceryl diisostearate, diglyceryl triisostearate, trimethylol propane trioctanoate, trimethylol propane triisostearate, and pentaerythritol tetraoctanoate.

The lipcolor composition according to the invention may be in a form of solid, liquid or powder.

The lipcolor in the form of solid preferably contains (a) 0.1 to 5 parts by weight, particularly 0.5 to 3 parts by weight, of the salt or hydroxide of divalent or trivalent metal, (b) 0.1 to 5 parts by weight, particularly 0.5 to 3 parts by weight, of the water-soluble salt of alginic acid, (c) 3 to 20 parts by weight, particularly 3 to 10 parts by weight, of the red or orange lake color having a COONa or COOK group in its structure, and (d) 15 to 45 parts by weight, particularly 15 to 30 parts by weight, of the oil component having appearance of liquid at a temperature of 20° C.

The lipcolor in the form of liquid preferably contains (a) 0.5 to 10 parts by weight, particularly 1 to 5 parts by weight, of the salt or hydroxide of divalent or trivalent metal, (b) 0.5 10 parts by weight, particularly 1 to 5 parts by weight, of the water-soluble salt of alginic acid, (c) 1 to 15 parts by weight, particularly 3 to 10 parts by weight, of the red or orange lake color having a COONa or COOK group in its structure, and (d) 15 to 98 parts by weight, particularly 20 to 50 parts by weight, of the oil component having appearance of liquid at 20° C.

The lipcolor in the form of powder preferably contains (a) 1 to 20 parts by weight, particularly 2 to 10 parts by weight, of the salt or hydroxide of divalent or trivalent metal, (b) 1 to 20 parts by weight, particularly 2 to 10 parts by weight, of the water-soluble salt of alginic acid, (c) 4 to 40 parts by weight, particularly 10 to 30 parts by weight, of the red or orange lake color having a COONa or COOK group in its structure, and (d) 15 to 35 parts by weight, particularly 15 to 30 parts by weight, of the oil component having appearance of liquid at 20° C.

The solid lipcolor of the invention may further contain conventional components, such as solid oil components, e.g., paraffins, ceresin and beeswax, pasty oil components, e.g., vaseline, lanolin and heavy liquid isoparaffins, liquid oil components, e.g., liquid paraffin and squalane, other organic coloring matters, inorganic pigments such as titanium oxide, antioxidants, preservatives and perfumes in addition to the aforesaid essential components, as long as these do not interfere with the pursuance of the purpose of the invention.

The liquid lipcolor of the invention may further contain conventional components, such as solid oil components, e.g., paraffins, ceresin and beeswax, oil-soluble thickening agents such as silicic anhydride, succrose esters of aliphatic acids and 12-hydroxy stearic acid, pasty oil components, e.g., vaseline, lanolin and heavy liquid isoparaffins, liquid oil components, e.g., liquid paraffin, squalane and silicone oils, other organic coloring matters, inorganic pigments such as titanium oxide, antioxidants, preservatives and perfumes in addition to the aforesaid essential components, as long as these do not interfere with the pursuance of the purpose of the invention.

The powder lipcolor of the invention may further contain conventional components, such as pigments, e.g., talc, mica, mica titanium, mica titanium treated with iron oxide, nylon powder and silk powder, solid oil components, e.g., paraffins, ceresin and beeswax, pasty oil components, e.g., vaseline, lanolin and heavy liquid isoparaffins, liquid oil components, e.g., liquid paraffin, squalane, dimethyl polysiloxane and methyl phenyl polysiloxane, other organic coloring matters, inorganic pigments such as titanium oxide, antioxidants, preservatives and perfumes in addition to the aforesaid essential components, as long as these do not interfere with pursuance of the purpose of the invention.

The present invention will be further explained in reference to the following unlimitative Examples.

EXAMPLES

In the Examples, the following evaluation item and method were adopted.

130 Female subjects were randomly grouped into 13 groups with each 10 members. Each group was provided with one out of 10 samples according to the invention and 3 samples for comparison. Each member puts her given lipcolor and, 2 hours later, ate Chinese foods which have a largest effect of removing lipcolor, and evaluated the lipcolor for its coming off.

Examples 1 to 10 and Comparative Examples 1 to 3

Solid lipcolors were prepared in a conventional manner using the components shown in Table 1 in the amounts shown in percent by weight. That is, components 1 through 14 were mixed and dissolved uniformly at 90° C., to which components 15 through 21 were added, kneaded and heat melted at 80° C. After deaeration, the mixture was poured in a mold and cooled to be shaped, and put into a receptacle to obtain a product lipcolor.

The results of the evaluation are as shown in Table 2, where the number of the people who answered that the lipcolor did not come off is indicated. Nobody had a dry or uneasy feeling 2 hours after the lipcolor was put in the Examples or the Comparion Examples, either.

TABLE 1

| | | Example | | | | | | | | | | Comparison Example | | | |
|---|---|---|---|---|---|---|---|---|---|---|---|---|---|---|---|
| | | 1 | 2 | 3 | 4 | 5 | 6 | 7 | 8 | 9 | 10 | 1 | 2 | 3 | 4 |
| 1 | Paraffin | 10.0 | 10.0 | 10.0 | 10.0 | 10.0 | 10.0 | 10.0 | 10.0 | 10.0 | 10.0 | 10.0 | 10.0 | 10.0 | 10.0 |
| 2 | Microcrystalline wax | 8.0 | 8.0 | 8.0 | 8.0 | 8.0 | 8.0 | 8.0 | 8.0 | 8.0 | 8.0 | 8.0 | 8.0 | 8.0 | 8.0 |
| 3 | Vaseline | 15.0 | 15.0 | 15.0 | 15.0 | 15.0 | 15.0 | 15.0 | 15.0 | 15.0 | 15.0 | 15.0 | 15.0 | 15.0 | 15.0 |
| 4 | Liquid paraffin d | B | B | B | B | B | B | B | B | B | B | B | B | B | B |

TABLE 1-continued

|  | Example | | | | | | | | | | Comparison Example | | | |
|---|---|---|---|---|---|---|---|---|---|---|---|---|---|---|
|  | 1 | 2 | 3 | 4 | 5 | 6 | 7 | 8 | 9 | 10 | 1 | 2 | 3 | 4 |
| 5 2-Octyl dodecanol | 20.0 | | | | | | | | | | 20.0 | | | |
| 6 Dioctyl adipate | | 20.0 | | | | | | | | | | | | |
| 7 Dioctyl succinate | | | 20.0 | | | | | | | | | | | |
| 8 Cholesteryl isostearate | | | | 20.0 | | | | | | | | | | |
| 9 Isononyl isononanoate | | | | | 20.0 | | | | | | | | | |
| 10 Ethylene glycol octanoate | | | | | | 20.0 | | | | | | | | |
| 11 Propylene glycol dicaprylate | | | | | | | 20.0 | | | | | | | |
| 12 Neopentyl glycol dioctanoate | | | | | | | | 20.0 | | | | | | |
| 13 Glycerin tri(caprylate/caprate) | | | | | | | | | 20.0 | | | 20.0 | | |
| 14 Trimethylolpropane triisostearate | | | | | | | | | | 20.0 | | | | |
| b |  |  |  |  |  |  |  |  |  |  |  |  |  |  |
| 15 Sodium alginate | 1.0 | 1.0 | 1.0 | 1.0 | 1.0 | | | | | | | | 1.0 | 1.0 |
| 16 Potassium alginate | | | | | | 1.0 | 1.0 | 1.0 | 1.0 | 1.0 | | | | |
| a |  |  |  |  |  |  |  |  |  |  |  |  |  |  |
| 17 Calcium sulfate | 1.0 | | 1.0 | | 1.0 | | 1.0 | | 1.0 | | | | 1.0 | 1.0 |
| 18 Ferrous hydroxide | | 1.0 | | 1.0 | | 1.0 | | 1.0 | | 1.0 | | | | |
| c |  |  |  |  |  |  |  |  |  |  |  |  |  |  |
| 19 Aluminium lake of D. & C. Red No. 28 (C.I. No. 45410) | 4.0 | 4.0 | 4.0 | 4.0 | 4.0 | 4.0 | 4.0 | 4.0 | 4.0 | 4.0 | 4.0 | 4.0 | 4.0 | |
| 20 D. & C. Red No. 7 (C.I. No. 15850) | | | | | | | | | | | | | | 4.0 |
| 21 Titanium oxide | 1.0 | 1.0 | 1.0 | 1.0 | 1.0 | 1.0 | 1.0 | 1.0 | 1.0 | 1.0 | 1.0 | 1.0 | 1.0 | 1.0 |

B: Balance

TABLE 2

|  | Example | | | | | | | | | | Comparison | | | |
|---|---|---|---|---|---|---|---|---|---|---|---|---|---|---|
|  | 1 | 2 | 3 | 4 | 5 | 6 | 7 | 8 | 9 | 10 | 1 | 2 | 3 | 4 |
| No coming-off | 8 | 8 | 8 | 9 | 8 | 8 | 10 | 8 | 10 | 8 | 0 | 5 | 3 | 0 |

Example 12

Liquid lipcolor with the following composition was prepared in a conventional manner, and subjected to a test as in Example 1. The results were good similarly.

| (d) | Diisostearyl malate | 10.0 wt. % |
|---|---|---|
| (d) | Pentaerythritol tetraoctanoate | 16.0 wt. % |
|  | Dimethyl polysilaxane | 3.0 wt. % |
|  | Silicic anhydride | 2.5 wt. % |
|  | Liquid paraffin | 58.1 wt. % |
| (b) | Sodium alginate | 2.0 wt. % |
| (a) | Calcium pantothenate | 2.0 wt. % |
| (c) | Aluminum lake of Eosine YSK (C.I. No. 45380) | 4.5 wt. % |
|  | Aluminum lake of F.D.& C. Blue No. 1 (C.I. No. 42090) | 0.5 wt. % |
|  | Yellow oxide | 1.4 wt. % |

Example 13

Powder lipcolor with the following composition was prepared in a conventional manner, and subjected to a test as in Example 1. The results were good similarly.

| (d) | Diglyceryl isostearate | 10.0 wt. % |
|---|---|---|
| (d) | Octyl oxystearate | 17.0 wt. % |
| (b) | Potassium alginate | 8.0 wt. % |
| (a) | Aluminum hydroxide | 5.0 wt. % |
| (c) | Aluminum lake of Phloxine BK (C.I. No. 45410) | 5.0 wt. % |
| (c) | Barium lake of D.& C. Red No. 28 (C.I. No. 45410) | 12.0 wt. % |
|  | Aluminum lake of F.D.& C, Blue No. 1 (C.I. No. 42090) | 0.5 wt. % |
|  | Barium sulfate | 5.0 wt. % |
|  | Mica | 17.5 wt. % |
|  | Mica titanium | 20.0 wt. % |

What we claim is:

1. A lipcolor composition comprising (a) at least one metal compound selected from the group consisting of salts of divalent and trivalent metals and hydroxides of divalent and trivalent metals, and (b) a water-soluble salt of alginic acid, and wherein the composition further comprises (c) at least one red or orange lake color with aluminum, barium or zirconium having a COONa or COOK group in its structure and (d) an oil component having appearance of liquid at a temperature of 20° C.

2. The lipcolor composition as claimed in claim 1, wherein the lake color (c) is an aluminium, barium or zirconium lake of D. & C. Red No. 28 (C.I. No. 45410); Rose bengal (C.I. No. 45440); D. & C. Red No. 22 (C.I. No. 45380); D. & C. Orange No. 11 (C.I. No. 45425); Eosine YSK (C.I. No. 45380); Phloxine BK (C.I. No. 45410); or Rose bengal K (C.I. No. 45440).

3. The lipcolor composition as claimed in claim 1, wherein the oil component which has appearance of liquid at a temperature of 20° C. is selected from the group consisting of monohydric alcohols having at least 16 carbon atoms; esters of monohydric alcohols having at least 3 carbon atoms or cholesterols with monobasic aliphatic carboxylic acids having at least 8 carbon atoms, adipic acid, oxystearic acid, succinic acid or malic acid; and esters of ethylene glycol, propylene glycol, neopentyl glycol, glycerin, diglycerin, trimethylol propane or pentaerythrytol with monobasic aliphatic carboxylic acids having at least 7 carbon atoms.

4. The lipcolor composition as claimed in claim 3, wherein the monohydric alcohols having at least 16 carbon atoms are isosteary alcohol, 2-octyl dodecanol, oleyl alcohol, 2-hexyl decanol and jojoba alcohol; the ester of monohydric alcohols having at least 3 carbon atoms or cholesterols with monobasic aliphatic carboxylic acids having at least 8 carbon atoms, adipic acid, oxystearic acid, succinic acid or malic acid are diisostearyl adipate, dioctyl adipate, isopropyl isostearate, cholesteryl isostearate, isononyl isononanoate, octyldodecyl erucate (ester of erucic acid), octyl oxystearate, cetyl octanoate, octyldodecyl oleate, oleyl oleate, dioctyl succinate, isocetyl stearate, isopropyl palmitate, octyldodecyl myristate, myristyl myristate, diisostearyl malate, decyl oleate, and octyldodecyl ricinoleate; and the esters of ethylene glycol, propylene glycol, neopentyl glycol, glycerin, diglycerin, trimethylol propane or pentaerythrytol with monobasic aliphatic carboxylic acids having at least 7 carbon atoms are ethylene glycol octanoate, ethyleneglycol palmitate, propylene glycol isostearate, propylene glycol ricinoleate, propylene glycol di(caprylate/caprate), propylene glycol dicaprylate, propylene glycol dimyristate, propylene glycol dicaprate, neopentyl glycol dioctanoate, neopentyl glycol dicaprate, glyceryl triisostearate, glyceryl diisoastearate, glyceryl trioctanoate, glyceryl tri (caprylate/caprate), glyceryl ricinoleate, diglyceryl isostearate, diglyceryl diisostearate, diglyceryl triisostearate, trimethylol propane trioctanoate, trimethylol propane triisostearate, and pentaerythritol tetraoctanoate.

5. The lipcolor composition as claimed in claim 1, wherein the lipcolor is in a form of solid and contains (a) 0.1 to 5 parts by weight of the salt or hydroxide of divalent or trivalent metal, (b) 0.1 to 5 parts by weight of the water-soluble salt of alginic acid, (c) 3 to 20 parts by weight of the red or orange lake color having a COONa or COOK group in its structure, and (d) 15 to 45 parts by weight of the oil component having appearance of liquid at a temperature of 20° C.

6. The lipcolor composition as claimed in claim 1, wherein the lipcolor is in a form of liquid and contains (a) 0.5 to 10 parts by weight of the salt or hydroxide of divalent or trivalent metal, (b) 0.5 to 10 parts by weight of the water-soluble salt of alginic acid, (c) 1 to 15 parts by weight of the red or orange lake color having a COONa or COOK group in its structure, and (d) 15 to 98 parts by weight of the oil component having appearance of liquid at a temperature of 20° C.

7. The lipcolor composition as claimed in claim 1, wherein the lipcolor is in a form of powder and contains (a) 1 to 20 parts by weight of the salt or hydroxide of divalent or trivalent metal, (b) 1 to 20 parts by weight of the water-soluble salt of alginic acid, (c) 4 to 40 parts by weight of the red or orange lake color having a COONa or COOK group in its structure, and (d) 15 to 35 parts by weight of the oil component having appearance of liquid at a temperature of 20° C.

8. The lipcolor composition as claimed in claim 1, wherein the water-soluble salt of alginic acid is sodium alginate, potassium alginate or ammonium alginate and a molecular weight of the alginic acid is 100,000 to 200,000.

9. The lipcolor composition as claimed in claim 1, wherein the salts of divalent or trivalent metals are calcium chloride, calcium carbonate, calcium lactate, calcium pantothenate, calcium sulfate, calcium citrate, calcium glycerophosphate, calcium gluconate, calcium hydrogenpyrophosphate, calcium biphosphate, calcium silicate, calcium stearate, calcium mesotartrate, calcium laurate, calcium acetate, aluminium sulfate, aluminium chloride, potassium alum, ferrous sulfate, ferric chloride, ferrous or ferric citrate, ferrous or ferric lactate, ferrous pyrophosphate, and sodium ferrous citrate; and the hydroxides of divalent or trivalent metals are calcium hydroxide, aluminium hydroxide and ferrous hydroxide.

* * * * *

UNITED STATES PATENT AND TRADEMARK OFFICE
CERTIFICATE OF CORRECTION

PATENT NO. : 6,197,284 B1
DATED : March 6, 2001
INVENTOR(S) : Nobumasa Sato

It is certified that error appears in the above-identified patent and that said Letters Patent is hereby corrected as shown below:

<u>Title page,</u>
The priority information is missing from the face of the patent. Please correct the title page, after [22] to read:

Item [30], Foreign Application Priority Data

August 6, 1992 (JP) .......................................4-233144

Signed and Sealed this

Thirtieth Day of October, 2001

*Attest:*

Nicholas P. Godici

NICHOLAS P. GODICI
*Attesting Officer*  *Acting Director of the United States Patent and Trademark Office*